(12) United States Patent
Ruben

(10) Patent No.: US 12,702,506 B2
(45) **Date of Patent: *Aug. 11, 2026**

(54) HEALTHCARE ASSISTIVE ROBOT APPARATUS

(71) Applicant: Geoffrey Lee Ruben, Washington, PA (US)

(72) Inventor: Geoffrey Lee Ruben, Washington, PA (US)

(73) Assignee: Geoffrey Lee Ruben, Washington, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/076,485

(22) Filed: Mar. 11, 2025

(65) Prior Publication Data

US 2025/0205000 A1 Jun. 26, 2025

Related U.S. Application Data

(63) Continuation of application No. 18/066,874, filed on Dec. 15, 2022, now Pat. No. 12,262,967.

(51) Int. Cl.

| | |
|---|---|
| ***A61B 34/32*** | (2016.01) |
| ***G06N 20/00*** | (2019.01) |
| ***G16H 50/20*** | (2018.01) |
| ***G16H 50/70*** | (2018.01) |

(52) U.S. Cl.

CPC ............. *A61B 34/32* (2016.02); *G06N 20/00* (2019.01); *G16H 50/70* (2018.01)

(58) Field of Classification Search

CPC ..... A61B 34/32; A61B 5/0077; A61B 5/1113; A61B 5/1128; A61B 5/165; A61B 5/4803; A61B 5/7267; A61B 5/746; B25J 11/0005; B25J 11/008; B25J 11/009; B25J 9/0003; B25J 9/163; B25J 9/1661; B25J 9/1697; G10L 15/22; G06N 20/00; G06V 10/811;

(Continued)

(56) References Cited

U.S. PATENT DOCUMENTS

2015/0359691 A1* 12/2015 Isozumi .................. A61G 5/04 180/19.1
2017/0020756 A1* 1/2017 Hillenbrand, II ..... A61B 5/1116
2018/0085055 A1 3/2018 Annoni et al.

(Continued)

FOREIGN PATENT DOCUMENTS

| | | | |
|---|---|---|---|
| CN | 111300451 A | | 6/2020 |
| EP | 3370175 A1 | | 9/2018 |
| KR | 20170135195 A | * | 12/2017 |

*Primary Examiner* — Hossam M Abd El Latif
(74) *Attorney, Agent, or Firm* — FERENCE & ASSOCIATES LLC

(57) ABSTRACT

One embodiment provides an assistive robot apparatus, the assistive robot apparatus including: a sensor system including at least one sensor that obtains input related to a health characteristic of a person under care of the assistive robot apparatus; an actuator system including at least one actuator that causes at least a portion of the assistive robot system to move and interact with an environment of the assistive robot apparatus; an analysis system that analyzes the input and provides instructions to the actuator system based upon the input; and an output system including at least one output device that communicates with at least one other system. Other aspects are described and claimed.

20 Claims, 8 Drawing Sheets

(58) Field of Classification Search
CPC ........ G06V 20/10; G06V 20/35; G06V 40/20; G06V 40/28
USPC .......................................................... 700/245
See application file for complete search history.

(56) References Cited

U.S. PATENT DOCUMENTS

| | | | | |
|---|---|---|---|---|
| 2019/0358822 | A1* | 11/2019 | Wojciechowski | G06F 18/256 |
| 2020/0023511 | A1* | 1/2020 | Lee | B25J 9/0084 |
| 2021/0053213 | A1* | 2/2021 | Lee | B25J 19/02 |
| 2021/0232934 | A1 | 7/2021 | Lai et al. | |
| 2022/0037039 | A1 | 2/2022 | Wein | |
| 2022/0409469 | A1* | 12/2022 | Shen | A63B 21/0058 |
| 2023/0046704 | A1* | 2/2023 | Yoder | A61B 5/7282 |
| 2024/0190013 | A1* | 6/2024 | Kim | G06Q 50/22 |
| 2024/0355479 | A1* | 10/2024 | Nakagawa | G06T 7/0016 |

* cited by examiner

HEALTHCARE ASSISTIVE ROBOT APPARATUS

CROSS-REFERENCE TO RELATED APPLICATIONS

This application is a continuation application of co-pending U.S. patent application Ser. No. 18/066,874, filed Dec. 15, 2022, entitles “HEALTHCARE ASSISTIVE ROBOT APPARATUS,” the contents of which are hereby incorporated by reference as if set forth in their entirety.

BACKGROUND

In the healthcare industry there are many different healthcare facilities and healthcare professionals that perform different functions. Some example healthcare facilities include long-term care facilities, short-term care facilities, acute-care facilities, emergency care facilities, healthcare systems, and/or the like. In addition to traditional healthcare facilities, some facilities offer some services that are similar to some services offered by traditional healthcare facilities, for example, assisted living facilities, senior care facilities, disabled persons care facilities, treatment facilities, charitable organizations, and/or the like. In addition to some healthcare treatments, some of these facilities may provide additional services to people living within them to allow the people to have as much independence while still maintaining the health and safety of the people. In other words, these facilities are generally set up so that a person can live as independently as the person is able, while still providing care for the activities that the person may need assistance with. All of these traditional healthcare facilities and other facilities that assist in caring for individuals require professionals and staff to assist in performing the functions of the facilities.

BRIEF SUMMARY

In summary, one aspect provides an assistive robot apparatus, the assistive robot apparatus including: a sensor system including at least one sensor that obtains input related to a health characteristic of a person under care of the assistive robot apparatus; an actuator system including at least one actuator that causes at least a portion of the assistive robot system to move and interact with an environment of the assistive robot apparatus; an analysis system that analyzes the input and provides instructions to the actuator system based upon the input; and an output system including at least one output device that communicates with at least one other system Another aspect provides a method, the method including: obtaining, using a sensor system of an assistive robot apparatus, input related to a health characteristic of a person under care of the assistive robot apparatus; analyzing, using an analysis system of the assistive robot apparatus, the input; providing, from the analysis system, instructions to an actuator system of the assistive robot apparatus based upon the input; interacting with an environment of the assistive robot apparatus in view of the input and by activating at least one actuator of the actuator system causing at least a portion of the assistive robot system to move based upon the instructions; and communicating, using at least one output device of an output system of the assistive robot apparatus, with at least one other system based upon the input.

A further aspect provides a product, the product including: a computer-readable storage device that stores executable code that, when executed by a processor, causes the product to: obtain, using a sensor system of an assistive robot apparatus, input related to a health characteristic of a person under care of the assistive robot apparatus; analyze, using an analysis system of the assistive robot apparatus, the input; provide, from the analysis system, instructions to an actuator system of the assistive robot apparatus based upon the input; interact with an environment of the assistive robot apparatus in view of the input and by activating at least one actuator of the actuator system causing at least a portion of the assistive robot system to move based upon the instructions; and communicate, using at least one output device of an output system of the assistive robot apparatus, with at least one other system based upon the input.

A further aspect provides a method, the method including: receiving, at a machine-learning model of an assistive robot system, input related to a health characteristic of a person under care; identifying a status of the person under care by analyzing the input utilizing the machine-learning model; and providing, from the machine-learning model, an output based upon the status.

A further aspect provides a method, the method including: receiving, at an assistive robot apparatus, at least one input related to a health characteristics of a person under care of the assistive robot apparatus; comparing, using the assistive robot apparatus, the at least one input to stored data related to health characteristics of the person under care; diagnosing, using the assistive robot apparatus, a condition of the person under care based upon the comparing; and providing, by the assistive robot apparatus, a diagnosis of the person under care identified based upon the diagnosing.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
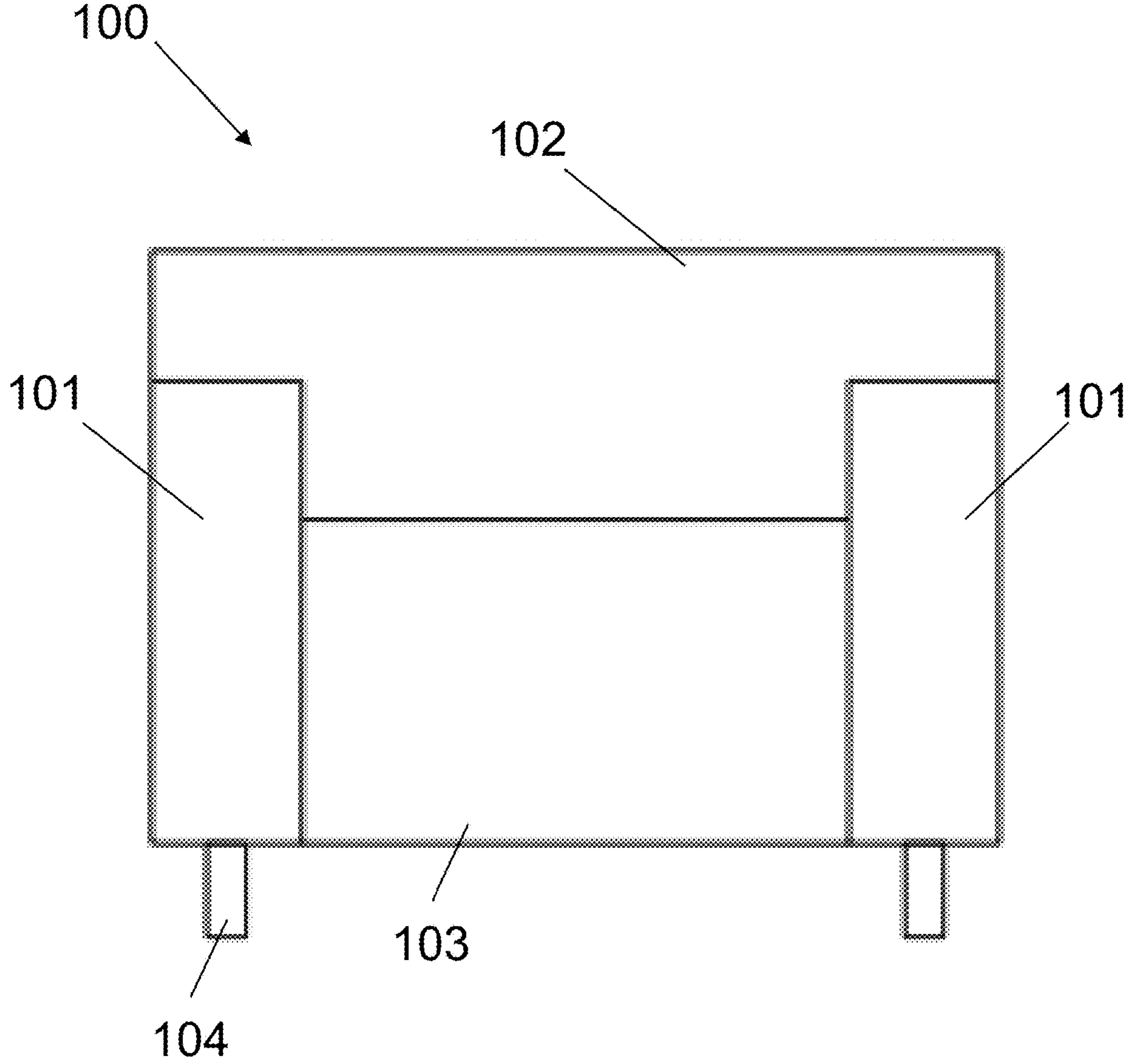
FIG. 1 illustrates an example of a front view of an assistive robot apparatus in a folded position.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

With as many people as may need assistance with at least one aspect of daily living, it can be easily understood that a large number of staff and professionals are needed to care for these people in both the traditional healthcare facilities and other living facilities. It can sometimes be difficult to find enough help to fully staff all of these facilities. Additionally, for certain aspects of living, a caregiver may need special qualifications, which can be even more difficult to find.

When attempting to place a person within a healthcare and/or other living facility, it can be difficult to find a place that has an occupancy for a person needing assistance, particularly a facility that may have amenities desired by the person needing to be placed there. Additionally, many people, particularly those that need assistance with one or a few aspects of daily living, do not want to leave their home. They would rather stay at home. Traditionally, those who want to remain in their home either have to hire assistance to come in and help with the aspects of daily living that they need assistance with, or they must have family in close proximity who are willing to come provide the necessary assistance. However, not all people are able to afford in-home healthcare or have family within close proximity that can assist with those daily living tasks. These people, while they could remain in their home if they had assistance with the few aspects of daily living, will need to be moved to a facility that can assist them.

Accordingly, the described system and method provides a system and method for an assistive robot system that can interact with a person under care of the assistive robot system based upon input related to a health characteristic of the person under care. The assistive robot system provides an assistive robot apparatus that includes a sensor system that includes at least one sensor that can obtain input related to a health characteristic of a person under care of the assistive robot apparatus. The sensor system may include sensors that are located on the assistive robot apparatus, sensors that are located directly on the person under care, sensors that are located on other objects, and/or the like. These sensors can capture information that may provide an indication regarding a health characteristic of the person under care including, for example, health metrics (e.g., oxygen saturation level, blood pressure, heart rate, respiratory rate, etc.), movements of the person under care (e.g., movements that might be indicative of imminent injury to the person under care, level of alertness, state of the person under care, etc.), audio of the person under care, gestures of the person under care, chemicals or other elements emitted by a person under care, magnetic changes in the person under care, and/or the like.

The assistive robot apparatus also includes an actuator system that includes at least one actuator that causes at least a portion of the assistive robot apparatus to move and interact with an environment of the assistive robot apparatus. The actuator system may allow the assistive robot apparatus to move within the environment and interact with the person under care. Additionally, the actuator system may allow the assistive robot apparatus to change from a first state to a second state. In other words, the actuator system may allow the assistive robot apparatus to transform from a first object shape to a second object shape. This may allow the assistive robot apparatus to perform multiple functions within an environment of a person under care. For example, a first state of the assistive robot system may be as a chair, which allows the person under care a place for sitting. When the person needs to stand, the assistive robot apparatus may transform to a standing state and, while transforming, assist the person to a standing position.

The assistive robot apparatus also includes an analysis system that analyzes the input and provides instructions to the actuation system based upon the input. The analysis system may include one or more machine-learning models, rules engines, historical data analysis systems, crowd-sourced data analysis systems, and/or the like, that can properly analyze the input to provide instructions to the assistive robot apparatus. The analysis system may also learn about the person under care over time, thereby allowing for the instructions to become unique to the person under care. The assistive robot apparatus also includes an output system that includes at least on output device that can communicate with at least one other system. For example, the output system may provide notifications to another person regarding a status of the person under care of the assistive robot system, provide output to a central system, provide instructions to another apparatus in an Internet of Things setting, and/or the like.

Accordingly, the assistive robot system has multiple systems that can each perform different functions of the overall system. For example, the system may include machine-learning models that can be used to analyze inputs received regarding a person under care and provide instructions to the assistive robot apparatus. These machine-learning models may be refined over time to become unique to the person under care. As another example, the system may include tools and analyses that allow for the monitoring and diagnosing of a person under care using the assistive robot apparatus.

The illustrated example embodiments will be best understood by reference to the figures. The following description is intended only by way of example, and simply illustrates certain example embodiments.

FIGS. 1-4 illustrate an example assistive robot apparatus that may be utilized in an assistive robot system. The assistive robot system may include a processor, memory device, output devices (e.g., display device, printer, communication devices, etc.), input devices (e.g., keyboard, touch screen, mouse, microphones, sensors, biometric scanners, etc.), image capture devices, and/or other components, for example, those discussed in connection with FIG. 8. While the assistive robot system may include known hardware and software components and/or hardware and software components developed in the future, the system itself is specifically programmed to perform the functions as described herein to interact with a person under care. Additionally, the assistive robot system includes modules and features that are unique to the described system.

The assistive robot system and the assistive robot apparatus may be utilized in different applications and may, therefore, take different form factors based upon the application. One application may be as an assistive robot in a healthcare facility. In this application, the assistive robot system and apparatus may be deployed to assist healthcare professionals in performing tasks related to patients or persons under care. For example, the assistive care apparatus may follow a healthcare professional and act as a second person when performing tasks related to the person under care, for example, lifting or maneuvering the person, assisting with daily living activities (e.g., bathing, eating, toileting, taking medications, dressing, etc.), and/or the like. This application is a little unique compared to the other applications because the assistive care apparatus would be programmed to assist multiple people under care, whereas in other applications it may be specific to a single person under care. However, even in these settings, one or more assistive robot apparatuses may be deployed or assigned to a single person under care, as described in connection with other applications.

In another application, the assistive robot system and apparatus may be deployed in a living facility or a home of a person under care. In this application one or more of the assistive robot apparatuses may be assigned to a specific person under care. Like in the healthcare facility example, the assistive robot apparatus may assist the person under care with maneuvering, daily living activities, and/or the like. In this application, however, the assistive robot apparatus may also monitor the person under care and act as a type of emergency apparatus that can identify if the person under care is about to suffer from injury, is suffering from an injury or illness, assist the person under care, and also summon additional assistance in the case it is needed. The assistive robot apparatus may also provide some form of companionship to the person under care. It should be noted that in facilities, multiple assistive care apparatuses may be deployed with some being assigned to specific persons under care and some being assigned to assist professionals and staff at the facilities, similar to those deployed in a healthcare facility.

The assistive robot system and apparatus may be deployed in other facilities or applications. For example, the assistive robot apparatus may be deployed in public locations and monitor for health crises, travel versions that allow the person under care to travel with the assistive robot apparatus, and/or the like. Thus, the assistive robot apparatus can assist many different types of persons under care, including, but not limited to, those persons under care who need minimal assistance to remain at home, long term persons under care who suffer from disabilities or long-term disease, pediatric persons under care, persons under care having acute or temporary needs for assistance, and/or the like.

The assistive robot system, also referred to as the system, may include different components, modules, objects, and/or the like, that work together to perform the functions as described in further detail herein. The assistive robot system may include an assistive robot apparatus, also referred to as the assistive robot or robot, that includes different systems. The assistive robot and associated systems will be discussed in further detail herein. The system may include a central system that can receive inputs, provide analyses, and/or provide outputs. The central system acts as a central hub or data hub for the assistive robot system. As a central hub, the central system may include or have access to different components that facilitate performance of different functions of the assistive robot system, for example, data storage, data analysis, data communication, data programming, and/or the like. The central system may also allow a point of access for one or more users to monitor and interact with the assistive robot(s) that are connected to the central system. This point of access also allows a user to access any data, communications, statuses, and/or the like, that the assistive robot has captured, learned, accessed, created, and/or the like, thereby allowing a user to monitor and glean information regarding the person under care.

The central system can communicate not only with the assistive robot or robots that are assigned to a specific person under care, but may also provide communication to other assistive robot systems that are assigned to other persons under care. Thus, the central system may include communication devices, for example, wireless communication devices, short-range communication devices, near-field communication devices, wired communication devices, network communication devices, and/or the like. The central system may also be able to communicate with other devices or components that may have communication abilities, for example, smart thermostats, smart appliances, network devices, smart blinds, internetwork devices, and/or any other device that may have communication capabilities. Thus, the central system may include components that allow for communication between the central system and the assistive robot(s) of the person under care, between the central system and other assistive robot systems, and between the central system and other components or devices that may be included in an environment of the person under care, for example, in an Internet of Things setting.

The central system may include one or more components that may be located on the assistive robot, at a location remote from the assistive robot, a combination thereof, and/or the like. For example, the robot may able to perform some analyses on-board and communicate the results thereof to another portion of the central system in a remote location. Thus, functions described as being performed by the assistive robot may be at least partially performed at the central system and functions described as being performed by the central system may at least be partially performed by the assistive robot.

The system may provide a software application that may include a graphical user interface, as described in more detail below. The software application may be accessible by a user via the central system. The software application may allow a user to program or interact with the assistive robot. Thus, a user may provide user input into the graphical user interface that can then be turned into instructions that can be received by the assistive robot. For example, a user may program the assistive robot with default settings, machine-learning models, information related to the person under care, a purpose or function of the assistive robot, and/or the like. While default settings may be utilized upon initial deployment of the assistive robot, the default values may be somewhat unique to the person under care. Default settings may be simple default settings that are utilized for any assistive robot serving the same purpose or function.

However, since the assistive robot is intended to serve a person under care, the assistive robot learns about the person under care. Accordingly, in order to at least partially jump-start this learning, the default values may be a little more unique to the person under care. One technique for creating default values that are a little more unique to the person under care is to initially program the assistive robot with default values that have been identified from a group of persons under care that have similarities to the target person under care. Since the central systems of the assistive robot systems are in communication with each other, the central systems may be able to identify similarities in characteristics of persons under care and group these persons under care into groups based upon the similar characteristics. It should be noted that in order to ensure privacy of the persons under care, the identifying information of the persons under care may be excluded from the data groupings or may be obfuscated within the data groupings so that an individual cannot be identified.

The system may employ one or more similarity measures to identify similarities between characteristics of individuals. For example, the system may employ cosine similarity techniques, distance similarity techniques, machine-learning similarity measurement techniques, combinations thereof, and/or the like. The system may apply one or more similarity techniques to different characteristics of persons under care to create groupings. Some characteristics that may be analyzed include gender, age, geographical location, health conditions, abilities, facility the person under care is located within, assistance needs of the person under care, and/or the like. Once the persons under care are grouped, the system can identify some settings that are common to those persons under care within a particular group. These common settings may be those that are common to all of the persons under care within the group or may be common to a certain number of the persons under care, majority of the persons under care, and/or the like. These common settings can then be programmed into the assistive robot apparatus for a person under care having characteristics similar to the group.

Other modified default settings can be identified using other techniques, for example, crowd-sourced information identifying common settings for persons under care, machine-learning models, secondary information sources, and/or the like. Secondary information sources may include healthcare resources, studies, condition informational material, news articles or news stories, social media sites, Internet sources, chat forums, and/or the like, that may provide insight into settings that may be beneficial for a person under care having one or more characteristics of the person under care. In order to analyze this information, the system may include one or more information parsers, information extractors, information analysis tools, and/or the like, to mine, parse, and analyze the information. Such tools may include audio parsers, image parsers, text parsers, information extractors, parts-of-speech analyzers, semantic analyzers, syntactic analyzers, entity classifiers, machine-learning models, and/or the like. The extracted information can then be correlated with person under care characteristics and possible settings of the assistive robot system and apparatus. Based upon this correlation, the system may identify settings that might be useful for the person under care based upon characteristics of the person under care.

Additionally, the graphical user interface may allow a user to view metrics, statistics, communications, received transmissions, transmitted transmissions, and/or the like, of the assistive robot or of the person under care of the assistive robot. For example, a user may view how many times the assistive robot has performed a particular task, how many times the person under care has suffered from an illness or condition (e.g., vertigo, dizziness, weakness, inability to walk, etc.), the frequency of updating the settings based upon learning by the assistive robot system or assistive robot, any communications or transmissions from the assistive robot system or robot to other devices within the environment, an overall assessment of the health of the person under care, a status of the person under care, how well the person under care is performing daily acts of living, patterns of the person under care, and/or the like.

This information may be accessible via the central system and may be stored in one or more data storage locations of the central system. Thus, the central system may include one or more data storage locations that may include data storage on the robot itself, data storage at the central system, data storage at a location remote to but accessible by the central system including, but not limited to, remote network data storage, cloud data storage, and/or the like, The graphical user interface may include different views that allow a user to access different portions of the central system and/or assistive robot system or interact with different functions of the central system and/or assistive robot system. Thus, the graphical user interface may provide tabs, icons, pull-down menus, search functions, and/or the like, that will allow the user to access different views. Different user and/or user roles may have different levels of access within the central system. Accordingly, not all views may be accessible by all users of the central system. Additionally, different information may be included in some views based upon the user and/or user role. To access the central system, a user may have to provide authentication credentials which not only act to prevent unauthorized users from accessing the system, but also to configure the graphical user interface for the authorized user and also to log the interactions the user has within the system.

The graphical user interface may include one or more graphical elements. The graphical elements may include user input fields that facilitate the access of different information within the system. The user input fields may also allow a user to provide input to view statistics; assistive robot commands, instructions, settings, communications, analyses, and/or the like; information regarding the person under care; and/or the like. Input fields may include radial selector buttons, pull-down menus, free-form fields, structured input fields, selection boxes, and/or any other type of input field. The graphical elements may include icons that a user can interact with.

Some icons may also be display icons that display information. The display icons may be static icons that have static visual elements. The display icons may be dynamic icons that have dynamic visual elements that change based upon an update in information displayed on the icon, periodically, based upon a condition being met, and/or the like. For example, the graphical element may be a display icon that displays the status of an assistive robot or overall status of a person under care. As the status is updated, the graphical element is updated to reflect the new status. In other words, the graphical element is iteratively updated based upon changes to the status of the assistive robot and/or person under care. As should be understood, there may be other dynamic graphical elements, and this is only an example of one. For example, other dynamic graphical elements may include other status indicators, statistic indicators, and/or the like.

Machine-learning models may be used by the assistive robot system, to perform many different functions. A machine-learning model, which may be a neural network, decision tree and/or forest, classifiers, random tree forest or classifier, a combination thereof, a combination of machine-learning models, and/or the like, may be utilized in performing one or more acts of the described system. For example, one or more machine-learning models can be used to identify persons under care having similar characteristics; learn habits, conditions, characteristics, and/or general information regarding a person under care; monitor for and diagnose medical conditions or injuries; predict potential injury-causing maneuvers; learn steps for performing different functions; learn when notifications needs to be sent and to whom they should be sent; learn when to transform from one state to another; learn when to provide instructions to other objects; and/or the like. It should be understood that while the terminology may refer to a single machine-learning model, multiple machine-learning models can be utilized in performing one or more functions of the recommendation system. The machine-learning model may include a plurality of layers, including input, output, hidden, a combination thereof, and/or the like, layers. The machine-learning model is very complex and utilizes complicated mathematical computations. Due to the complexity of the machine-learning model, it would be impossible to perform the analysis as performed by the model in the human mind.

Additionally, the machine-learning model is trained to or utilized to make predictions on data that has been previously unseen by the model. To make these predictions, the model includes very complicated mathematical computations that would not be performed in the human mind. Rather, the use of a computer and processor, and, possibly a computer and processor that is specific and tuned to the machine-learning model, allows for performing these complex computations, particularly with a speed that allows for performing the complex processing found in and required by the machine-learning model in a time frame that facilitates the use of the machine-learning model for making the predictions. This speed is not possible with a human or even a group of humans. Thus, a human or even a group of humans, even using pen and paper, could not perform the analysis performed by the machine-learning model in a manner that would actually result in making the predictions provided by the machine-learning model on the large amount of data that is received by the assistive robot system in a length of time that would make the assistive robot system function as intended.

The machine-learning model may be trained using a training dataset having annotated training data. Annotated training data includes data that the model may make a prediction upon where the data is annotated with the correct prediction. The machine-learning model can learn from the training dataset how data should be classified or the predictions that should be made with respect to particular data. As predictions are made upon non-annotated data, feedback may be provided. Feedback may be provided in the form of a user making a correction, a user providing input regarding the prediction, predictions from other models regarding the same data, and/or the like. The feedback can be automatically ingested by the model to further train the model, thereby making the model more accurate over time. It should be noted that the model can monitor the predictions made by the model to identify the feedback so that a user does not have manually provide the feedback to the model. Thus, while the model may initially be trained with a training dataset, the model can continually be trained as it is deployed using predictions and feedback regarding the predictions.

In the case of learning settings to be utilized for a particular person under care, the machine-learning model may be trained using settings data correlated with persons under care and may, therefore, be able to perform functions for persons under care. As the assistive robot system is deployed, the system learns different information about the person under care, which can be ingested as feedback into the machine-learning model, thereby refining the machine-learning model and making it unique to the person under care. Over time, the model will become very unique to the person under care, and the assistive robot system will be able to anticipate needs of the person under care and also learn when the person under care may be suffering from a health condition, among other things. This allows the assistive robot system to take action to assist the person under care in a manner that is best suited for the person under care. Similar training and corresponding predictions may be used for other portions of the described system. The machine-learning model also be trained using unsupervised learning techniques, other supervised learning techniques, reinforcement training, a combination thereof, and/or the like.

The assistive robot apparatus may be a robot device that can take on different appearances based upon the application for which it is deployed. Different appearances may include more humanoid appearances, object-like appearances, animal-like appearances, robot-like appearances, and/or the like. In addition to taking on different appearances, the robot may be able to transform from one state to another. For example, the robot may take on a first state that is reminiscent of a furniture piece or other object shape. As the robot detects that a person under care needs assistance, the robot may transform from the first state to a second state that corresponds to a state from which the robot may provide assistance. While a first state and a second state is noted, it should be understood that the robot can transform to other states, either being iterative states between the first state and the second state or a completely different state, for example, transforming from the second state to a third state.

Figure 2:
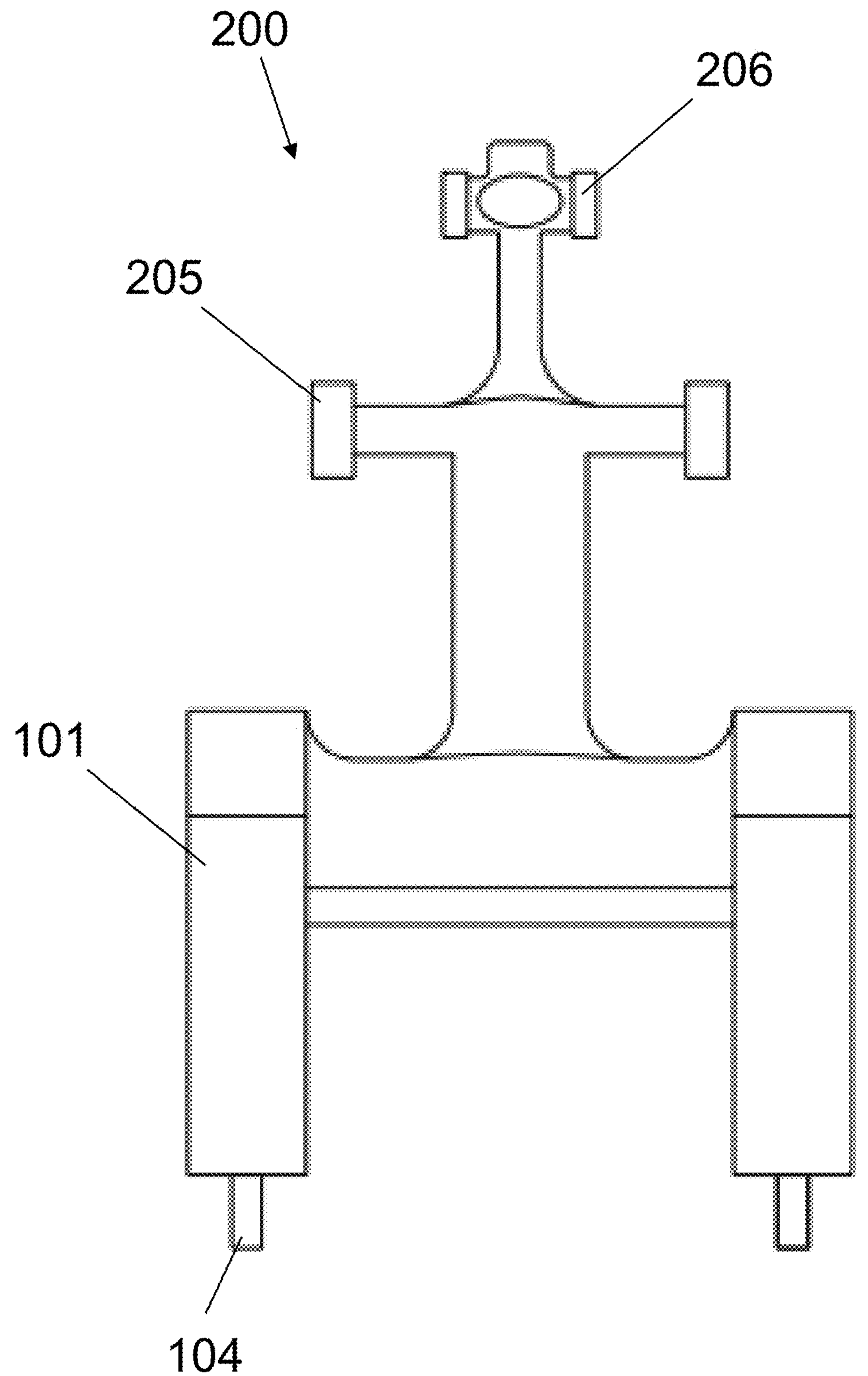
FIG. 2 illustrates an example of a front view of the assistive robot apparatus of FIG. 1 in a fully extended position.
Figure 3:
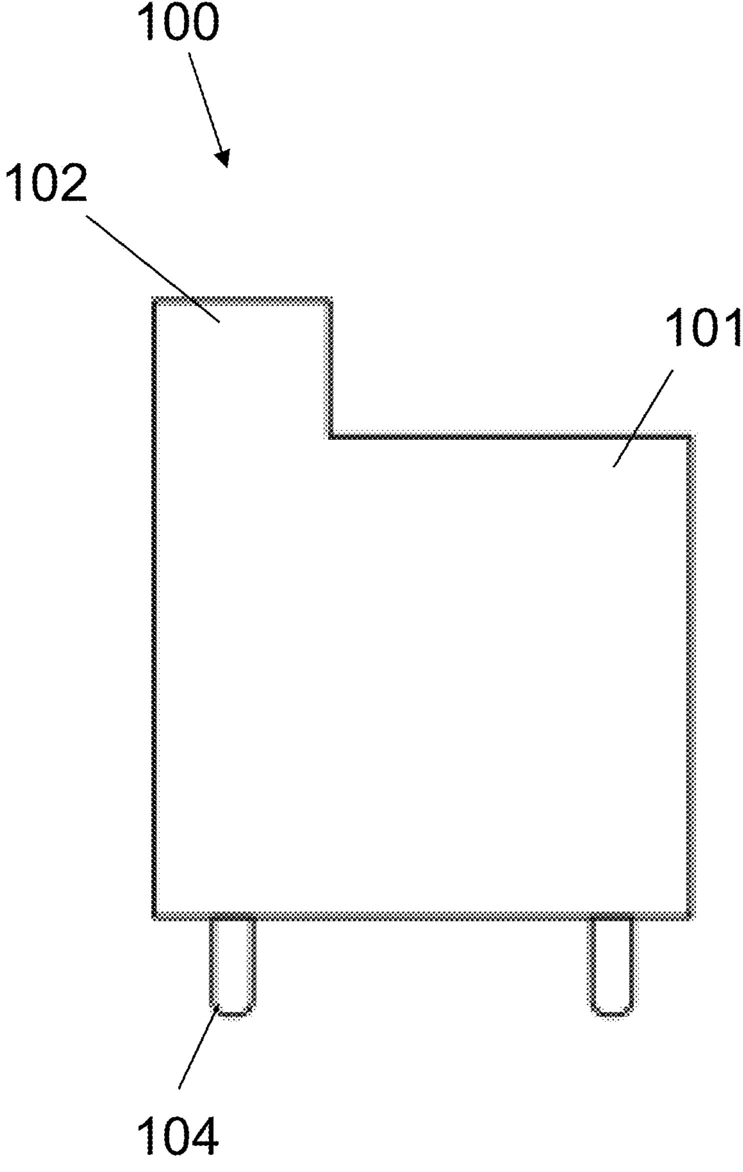
FIG. 3 illustrates an example of a side view of the assistive robot apparatus of FIG. 1 in the folded position.
Figure 4:
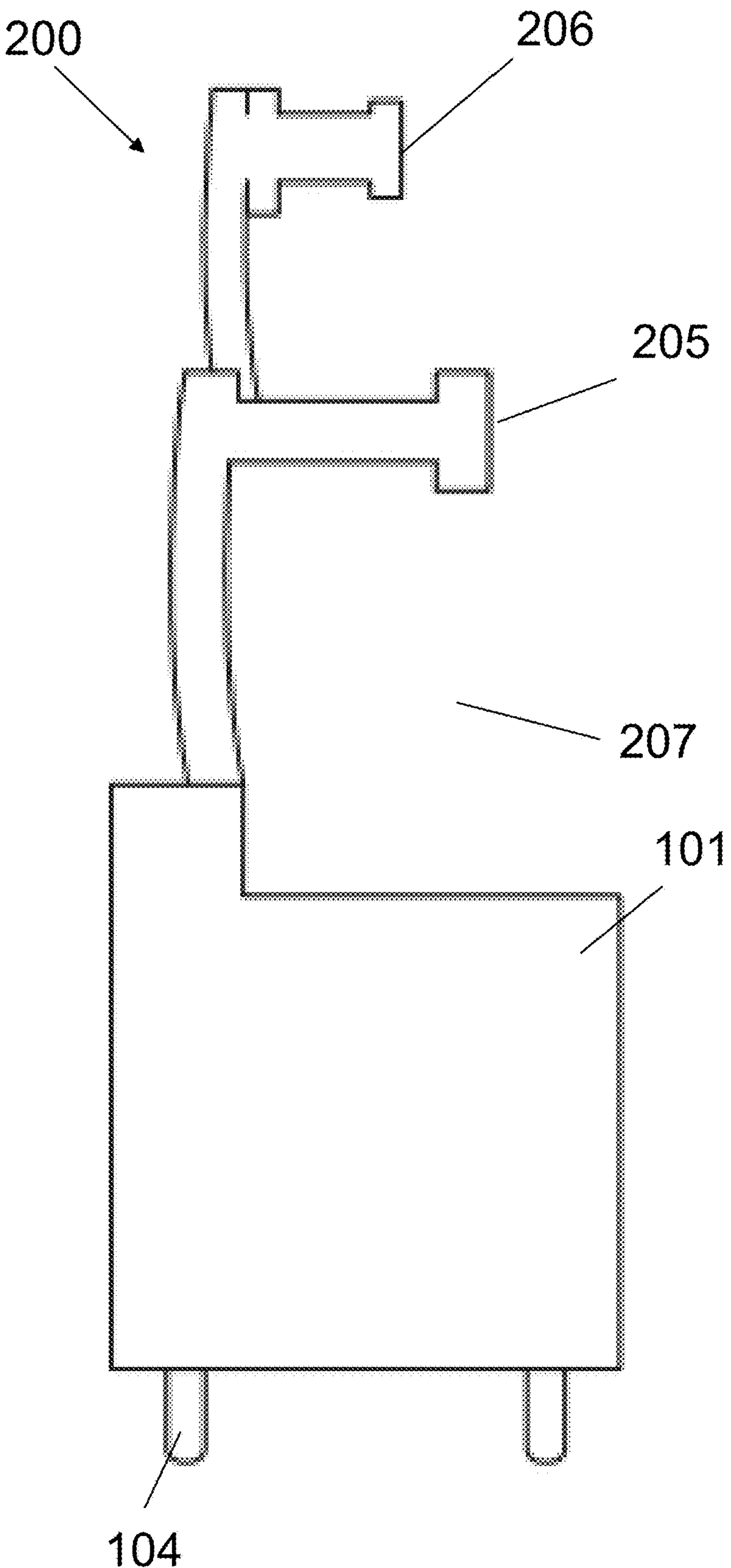
FIG. 4 illustrates an example of a side view of the assistive robot apparatus of FIG. 2 in the fully extended position.

As an example, FIGS. 1-4 illustrate an example assistive robot that transforms from a first state to a second state. In this example, the robot transforms from a chair to a standing robot. FIG. 1 illustrates a front view of the robot folded in the first state of the chair. FIG. 2 illustrates the same front view of the robot, but in a fully extended state. FIG. 3 illustrates a side view of the folded state of FIG. 1 and FIG. 4 illustrates a side view of the fully extended state of FIG. 2. When the robot detects that a person under care needs assistance, it can extend from the chair state of FIG. 1 and FIG. 3, to the standing robot or fully extended state of FIG. 2 and FIG. 4. In the chair state, the person under care can use the robot to sit upon or otherwise use it as a chair. However, when the robot detects the person under care needs assistance, will need assistance, or that the robot should otherwise transform, the robot can transform to the standing robot state. If the person is sitting in the chair at the time of transformation, the robot can guide the person under care into a standing position. Additionally, in this standing state, the robot can assist the person under care with one or more tasks, for example, walking, dressing, bathing, and/or the like.

As another example, not illustrated, the assistive robot may take the form of a bedside table in a first state. The person under care can utilize the bedside table as a table. When the robot detects that the person under care needs assistance, the robot can transform into a different state, for example, one that has arms that can maneuver the person under care, that allows the robot to assist the person under care. Other forms are contemplated and possible, as many different forms may be useful for a person under care. Other, non-limiting examples, include a couch or bed robot that transforms to a standing robot or that includes arms or other appendage-like parts that would allow the robot to maneuver the person under care on the couch or bed to assist with garment changing, dressing, bathing, prosthetic changes or attachments, and/or the like; an ottoman robot that can extend arms to help clean a person; a rug robot that can lift a person under care; a lamp robot that can maneuver a person under care; a humanoid robot that can carry things for the person under care and dispense medication for the person under; and/or the like.

The assistive robot apparatus may include multiple systems. Some of these systems may be located on the assistive robot apparatus itself, may be located at the central system, may be located on a different object in communication with the assistive robot apparatus, may be located at a combination thereof, and/or the like. One system may include a sensor system that can obtain input related to a health characteristic of a person under care of the assistive robot apparatus. The sensor system may include one or more sensors that can obtain the input. The sensors may be located on the robot itself, on the person under care, on other objects in communication with the robot or robot system, a combination thereof, and/or the like.

For example, the robot may be equipped with sensors that can directly or indirectly capture the input. As another example, the person under care may wear sensors or objects that have sensors that can provide information to the robot. For example, the person under care may have a smart watch, smart pendant, smart garments, and/or the like, that include sensors that can provide input to the system. As a final, non-limiting example, objects within the environment may be equipped with sensors that can provide input to the system. For example, the environment may include smart appliances, smart thermostats, motion detectors, smart lights, cameras, microphones, carbon monoxide detectors, and/or the like, that can capture information regarding the environment or person under care and provide these inputs to the system. The objects within the environment may be connected together in an Internet of Things setting where the objects can communicate with each other, can work together to perform analyses, and can work together to perform functions.

Input related to a health characteristic may be any number of inputs that can be analyzed to determine a health characteristic of the person under care. Health characteristics may include health metrics including physical qualities, for example, heart rate, blood pressure, oxygen saturation level, respiration rate, pupil dilation, reaction to light, and/or the like. Health metrics may also include the ability to detect a health state of a person under care, for example, illness, disease, normal, and/or the like, through non-physical qualities, such as chemicals emitted by breathing, perspiration, waste, and/or the like, magnetic changes that may be indicative of a change in the person under care, electrical changes that may be indicative of a change in the person under care, and/or the like.

Health characteristics may also include movements and speech of the person under care. For example, is the person under care moving normally, appearing to move into a state that may be indicative of an injury or potential injury, slurring speech, incoherent speech, and/or the like. Other health characteristics may include gestures, chromosome alterations, and/or the like. Accordingly, example sensors may include, biometric sensors, heart rate sensors, respiration sensors, oxygen saturation level sensors, blood pressure sensors, movement sensors, accelerometers, gyroscopes, proximity sensors, gesture sensors, microphones, infrared sensors, heat sensors, temperature sensors, light sensors, chemical detection sensors, magnetic change sensors, image capture devices, and/or the like.

The assistive robot apparatus may include an actuator system that includes at least one actuator that can cause at least a portion of the robot to move and interact with an environment of the assistive robot apparatus. The environment not only includes physical objects within the environment (e.g., lamps, desks, chairs, cabinets, utensils, appliances, beds, rugs, plates, food, liquids, thermostats, fans, curtains, etc.), but also includes the person under care and any non-physical objects, for example, wireless communications, the air, and/or the like. In other words, the robot can interact with the environment in a manner similar to how a person would interact within the environment. Additionally, the robot can send transmissions to and/or receive transmissions from other objects within the environment.

Thus, the robot may be equipped with actuators that allow the robot to move in ways that allow interaction with the environment, including the person under care. Actuators may include wheels, pistons, switches, pumps, and/or the like. Additionally, the actuator system may include components that facilitate the movement of the actuators, including, hydraulic systems, air systems, water systems, pumps, switches, electrical systems, combustion systems, and/or the like. The actuator system can be utilized within the robot to move one or more parts of the robot. This may include actuating a system to move an appendage, the whole robot, doors on the robot, pinchers, finger-like appendages, swivel the robot, and/or the like.

The actuator system may be utilized in moving the robot from a first state to a second state. Multiple actuators or actuator sub-systems may work in coordination to perform movements of the robot and perform different functions. For example, if the robot is attempting to turn a patient from a prone state to a laying on a side state, both arms of the robot may need to work together to gracefully maneuver the person under care without harming the person under care. This coordination and the movements required to perform any function of the robot may be programmed into the robot. Additionally, the robot may learn movements over time, for example, utilizing one or more machine-learning models, to make movements that are more suited to the person under care. Determining the movements to make can be performed by an analysis system of the robot which provides instructions to the robot and the actuator system to move the robot.

The analysis system may analyze the input to generate and provide instructions to the actuator system based upon the input. In other words, based upon a need of the person under care, as determined from the input, the analysis system identifies how the robot may be useful to or perform a function for the person under care, and then provides instructions to the actuator system to cause the robot to perform the movements to facilitate the usefulness or the performance of the function. To identify a need of the person under care, the analysis system may determine a status or state of the person under care through analysis of the input.

The status or state of the person under care may refer to a position of the person under care in the context of the environment of the person under care. Thus, the status or state may refer to a health status of the person under care (e.g., normal, suffering from a health episode, in a state possibly leading towards injury, etc.), a state of the person under care (e.g., sleeping, sitting, eating, bathing, etc.), a position of the person under care (e.g., prone, laying on side, sitting in an upright position, reclined, hunched over, falling, etc.), a location of the person under care with respect to the environment (e.g., bedroom, kitchen, on the floor, in a laundry room, etc.). As should be understood, the combination of states of the person under care and the context of the environment may be indicative of different issues. For example, a person under care laying in bed may be indicative of the person under care being in a normal or non-event state. On the other hand, if the person under care is laying on the floor, this may be indicative of a problem or issue that needs addressed.

One technique for performing the analysis is to compare or analyze the input against a datastore of inputs unique to the person under care. As the assistive robot system interacts with the person, the assistive robot system can receive and store information that is unique to the person under care, for example, habits, observations, normal conditions of the person under care, health conditions and observations thereof, and/or the like. This information may be stored in a datastore to be accessed at a later time.

The datastore may also be populated with information regarding the person under care obtained from sources other than the assistive robot system. For example, a healthcare provider, family member, person under care themselves, a person monitoring the person under care, and/or the like, may upload or add information regarding the person under care to the datastore. Information that may be added may include, but is not limited to, health condition updates, medications, observations of the person under care, testing results, person under care habits, person under care preferences, and/or the like. Essentially, any information that would be helpful for assisting the person under care, can be stored within the datastore.

Generally, each of the information stored within the datastore can be broken into a value or rule. For example, health metrics can be stored as values or value ranges. As another example, observations or preferences can be stored as a rule. It should be noted that not all information within the datastore has to be stored as a value and/or rule. Rather, this explanation is intended to further the understanding of the system described herein. However, since the system is highly sophisticated, information can be stored in different formats or manners and still be used by the system for analysis. When the system receives an input, the system can analyze the input against the appropriate information within the datastore. In the case of a value, the system can analyze the input against the value and determine whether the input falls within the desired value.

For example, the system may determine if the input falls within a predetermined threshold. Input falling outside the predetermined threshold may indicate an abnormal condition with the person under care. The robot may then take action with respect to the abnormal condition. The action may include activating different actuators to cause the robot to move to account for the abnormal condition. For example, if the input indicates that the person under care is dizzy or likely to fall, the analysis system can analyze the input, make the determination that the person under care may fall, and cause the robot to move into a position to catch the person under care and move the person under care into a safe position. As another example, if the input indicates that the person under care needs to take medication, the analysis system can analyze the input, make the determination that the person needs to take medication, and cause the robot to access the medication and give it to the person under care.

There may be situations where a single input is not outside a predetermined threshold, but an aggregation of inputs, all within a predetermined threshold, may indicate an abnormal condition. In other words, there may be situations where the fact that a person under care is exhibiting a multitude of symptoms, which on their own would not be indicative of an issue, is an indication of an issue with the person under care. The system is able to make this determination and take action to account for or correct the issue. In conjunction with the values comparison, the system may utilize a rules engine that provides decisions based upon the input. A rules engine may be programmed with different rules that cause a different action by the robot based upon the input received. For example, if the input indicates that a person is awaking from a sleeping state, the rules engine may indicate that the robot needs to move to an assistive state instead of a folded state. Using the example, of FIGS. 1-4, the assistive state would be the unfolded stated. The rules engine may also be used with the values. For example, the input values may be fed to the rules engine to output a decision or action.

As previously noted, the system learns about the person under care, so the values and rules engine can become refined for the person under care. As an example, for a person suffering from restless leg syndrome, leg movements during sleep may be common and no cause for alarm by the system. However, a person under care who does not suffer from restless leg syndrome and makes sudden uncontrolled movements with their legs while sleeping, may cause the robot to take action to assist the person under care. Thus, the rules engine and values cause decisions and actions by the robot that are unique to the person under care. Additionally, the system may utilize a machine-learning model that is also refined over time to become unique to the person under care, to make decisions and cause actions by the robot. Thus, even though the machine-learning model is initially trained, it becomes retrained and refined over time based upon inputs of the person under care, actions and decisions taken by the system in response to these inputs, and feedback provided in response to those actions and decisions. The machine-learning model can then be utilized by the analysis system to provide instructions to the robot based upon the person under care.

As the robot learns new things, the robot can also address some medical emergencies, illnesses, conditions, and/or the like. The robot can render first aid, perform some medical treatments (e.g., perform CPR, perform the Heimlich maneuver, utilize a defibrillator, etc.), treat illnesses or conditions, and/or the like. Learning treatments may be performed utilizing machine-learning models, historical information, secondary information sources, combinations thereof, and/or the like.

While the analysis system has, up to this point, been discussed as responding to inputs to help the person in the event of an illness, disease, injury, or other event, the analysis system can also be utilized to assist the person under care, even when the person under care is not under distress or is not about to be under distress. Rather, the robot is intended to not only respond to events to assist the person under care, but is also intended to assist the person under care with daily living tasks so the person under care can remain as independent as they want to be, while still maintaining their safety. Additionally, the robot can also act as a companion to a person under care.

Thus, the analysis system can analyze inputs to identify when the person under care needs assistance with a daily living task or might need just a little assistance. For example, the analysis system can analyze the inputs and determine the person under care is attempting to move from a sitting position to a standing position. The analysis system can then provide instructions to the actuator system to cause the robot to assist the person to the standing position. In the case that the robot is a chair and the person under care is sitting in the chair, this may include moving from the chair state to a standing robot state while moving the person with the robot into a standing position. As another example, the analysis system may analyze the input and determine the person under care is attempting to get dressed. The analysis system can provide instructions to the actuator system to assist the person with dressing. As a final, non-limiting example, the analysis system can analyze the input to determine the person is waking. The analysis system can activate the robot to be in a ready state to assist the person in maneuvering out of bed when the person does wake.

The robot can also respond to commands by the person under care or a person assisting the person under care. The person under care or another person can issue audible commands, gesture commands, and/or the like, to the system which can be analyzed by the analysis system to identify the command and then perform the action(s) corresponding to the command. As can be understood, different persons under care may have differing degrees of communication ability. For example, some persons under care may be unable to speak, coherently speak, move different body parts, and/or the like. Thus, different modalities of commands can be understood by the system.

For example, the system may be equipped with sensors that can read electrical signals (e.g., electrocardiogram, electromyography, etc.) that can be translated into small movements or even thoughts made by the person under care, which can then be translated into a command to the assistive robot system. As another example, the system may be equipped with facial recognition software or eye gaze tacking software that can detect small movements of the face or eyes that can be translated into commands. For example, gaze tracking software may be utilized to identify a location on a keyboard or other input device that a person under care is looking to identify a command the person is attempting to provide.

Whatever input modality is used, the assistive robot system may be programmed with commands that correspond to a function. Thus, upon receiving the command, the system can cause the robot to perform the function associated with the command. As an example, the person under care may provide a command that corresponds to a help function, which causes the robot to assist the person under care with whatever action the person under care is performing at the moment and/or to summon assistance in the event the system determines the person under care is suffering from a health episode that the system is unable to correct. As another example, the person under care may provide a command that corresponds to the robot performing a specified function, for example, making a meal for the person under care, getting a drink for the person under care, playing music for the person under care, reading a book to the person under care, providing medication to the person under care, and/or the like. The system then analyzes the command and performs the function corresponding to the command. As previously mentioned, these commands may be specific to the person under care due to programming or learning about the person under care over time.

It should be noted that the system can override some commands in the event the analysis system determines that performance of the command may put the person under care or another person in the way of harm.

In addition to receiving commands from users, the robot can also communicate with the person under care or other users. These communications may be using any type of output, for example, audible outputs, display outputs, notifications, gesture outputs, and/or the like. Thus, the robot may be equipped with components that allow for this communication, such as speakers, displays, appendages that provide gestures, and/or the like. This allows the robot to be more “human-like” and communicate with the person under care like a companion. This also allows the person under care to be more aware of what is happening. Additionally, if the robot has a question or is unsure of whether the person under care may need assistance, the robot can communicate with the person under care and the person under care may be able to provide confirmation that assistance is needed.

The assistive robot apparatus also includes an output system that includes at least one output device that can communicate with at least one other system. In other words, the output system operates to provide outputs to a system other than the robot or assistive robot system, even though these outputs may be facilitated by or through the robot or robot system. The output device may include any communication device or transmission medium, for example, wired connection, wireless communication device (e.g., near-field communication device, short-range communication device, network communication device, internetwork communication device, etc.), network connection devices, display device, printer, facsimile machine, and/or the like.

As previously mentioned, the assistive robot system can be interconnected with other objects or devices (e.g., via an Internet of Things setting, through wired or wireless communications, etc.), other assistive robot apparatuses, other assistive robot systems, and/or the like. Thus, the output device can be utilized to provide instructions or output to one of the connected objects or devices, other robots, other robot systems, and/or the like. The output may include instructions to perform some function, for example, turn on a furnace, turn on a light, open blinds, work collaboratively with the robot to perform a function for the person under care, and/or the like.

The output may also include notifications or alerts that may be related to the person under care. For example, if the robot or robot system identifies the person under care is suffering from a health episode, needs assistance, needs a reminder, needs a function to be performed at a particular time, and/or the like, the robot or robot system may provide an alert or notification to another object, robot, robot system, and/or the like, in the event that these objects or other robots can assist with addressing the alert or notification. In addition to providing output to other objects, robots, robot systems, and/or the like, the system may provide output to a human. The human may be a family member, healthcare provider, facility staff member, emergency care personnel, friend, system coordinator, and/or the like.

The output to the human may be in the form of an alert or notification depending on the urgency of the output. For example, if the person under care is under duress or suffering from a medical episode, the output may be in the form of an alert indicating the person under care needs human intervention. As another example, if the person under care simply wants to send a message to a human, the output may be in the form of a notification. Other notifications may be related to reminders, update of health metrics, diagnoses identified by the robot, statistics, observations, and/or the like. In the case that the person under care may need medical intervention, the system may summon emergency medical personnel, for example, by dialing 9-1-1, accessing an emergency alert network, and/or the like.

The output can be in any output form and may include, but is not limited to, a transmission to a device of a human (e.g., text message, alert notification, telephone call, pager transmission, etc.), transmission to a social media site of a human, update of a health record, update of a graphical user interface, transmission to an output device (e.g., facsimile machine, printer, etc.), and/or the like. How the output is provided may be based upon preferences of the person receiving the transmission. Additionally, the system may learn the best technique for contacting an individual over time as communications are provided and responded to.

Figure 5:
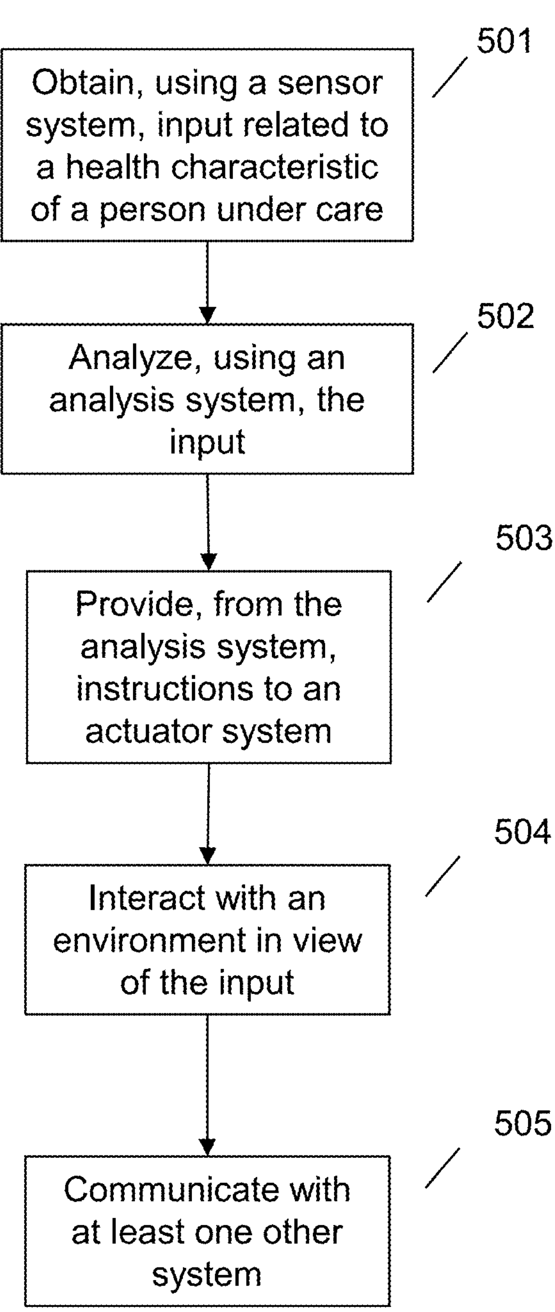
FIG. 5 illustrates an example method of utilizing an assistive robot apparatus to interact with a person under care based upon health characteristics of the person under care.

FIG. 5 illustrates a method for utilizing an assistive robot apparatus to interact with a person under care based upon health characteristics of the person under care. A sensor system of the assistive robot apparatus may obtain input related to a health characteristic of a person under care of the assistive robot apparatus at 501. At 502, the analysis system of the assistive robot apparatus analyzes the input to identify some instruction that corresponds to the input. Once the analysis has been performed, the analysis system provides instructions to an actuator system of the assistive robot apparatus based upon the input at 503. At 504, the assistive robot apparatus interacts with the environment of the apparatus in view of the input and by activating at least one actuator of the actuator system. This activation causes at least a portion of the robot system to move based upon the instructions. The assistive robot apparatus also communicates, using an output device of an output system, with at least one other system based upon the input at 505.

Figure 6:
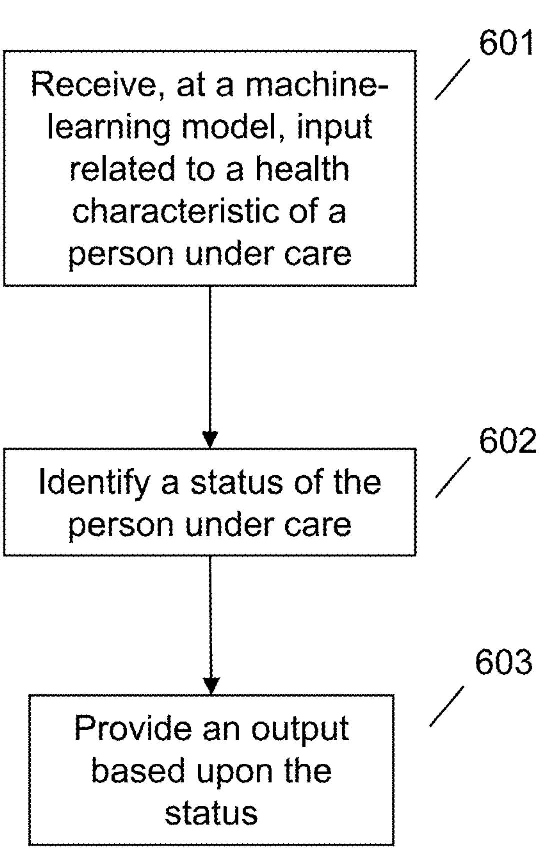
FIG. 6 illustrates an example method of utilizing a machine-learning model to identify a status of a person under care of an assistive robot system.

FIG. 6 illustrates an example method of utilizing a machine-learning model to identify a status of a person under care of an assistive robot system. A machine-learning model of the assistive robot system may receive input related to a health characteristic of a person under care at 601. The machine-learning model may be a portion of the analysis system of the assistive robot system and previously described. Additionally, as previously described, the machine-learning model may be initially trained utilizing annotated data and may be refined over time to become a model unique to the person under care. The machine-learning model may be trained to identify a status of the person under care through analysis of the input. Thus, at 602, the machine-learning model may be utilized to analyze the input and identify a status of the person under care. The status may be any status as was previously described. From the identified status, the machine-learning model provides an output at 603. The output may be any of the outputs as previously described, including outputs from the output system, output to the assistive robot or assistive robot system, outputs to other devices or systems, and/or the like.

Figure 7:
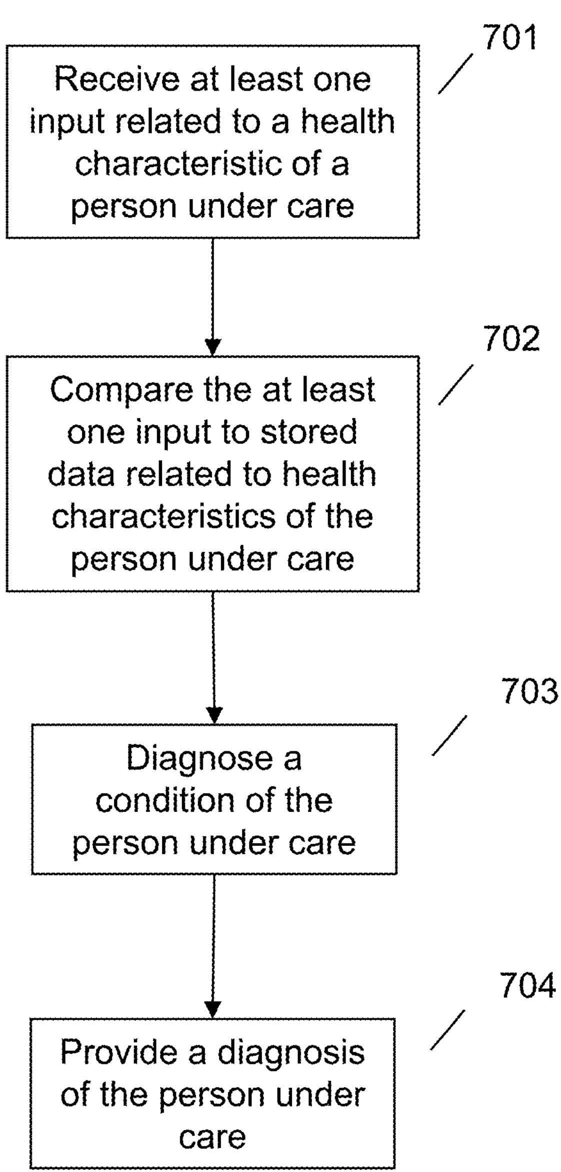
FIG. 7 illustrates an example method of diagnosing a person under care of an assistive robot apparatus using the assistive robot apparatus.

FIG. 7 illustrates an example method of diagnosing a person under care of an assistive robot apparatus using the assistive robot apparatus. At 701, the assistive robot apparatus may receive at least one input related to a health characteristic of a person under care of the robot. At 702, the robot apparatus may compare the at least one input to stored data related to health characteristic of the person under care. From the comparison, the robot apparatus may diagnose a condition of the person under care at 703. The diagnosing may be conducted using the analysis system and any of the techniques described herein. Once the diagnosis is made, the robot may provide the diagnosis to a human at 704. The diagnosis may also be provided to the robot system so that stored information may be updated, the robot system can take any necessary action, an output can be provided, instructions can be generated for the robot, and/or the like.

Figure 8:
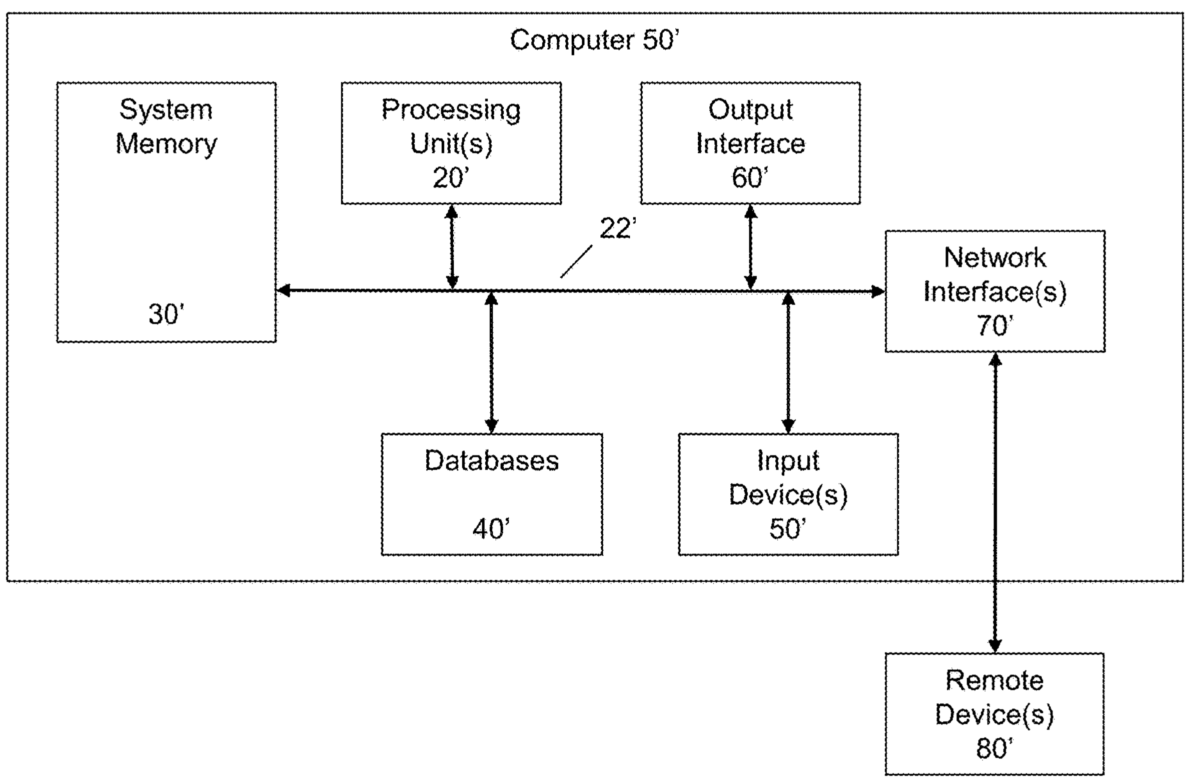
FIG. 8 illustrates an example of device circuitry.

While various other circuits, circuitry or components may be utilized in information handling devices, with a computer, server, client device or the like, an example device that may be used in implementing one or more embodiments includes a computing device in the form of a computer 10' as illustrated in FIG. 8. This example device may be a server used in one of the systems in a hospital network, or one of the remote computers connected to the hospital network. Components of computer 10' may include, but are not limited to, a processing unit 20', a system memory 30', and a system bus 22' that couples various system components including the system memory 30' to the processing unit 20'. Computer 10' may include or have access to a variety of computer readable media, including databases. The system memory 30' may include non-signal computer readable storage media, for example in the form of volatile and/or nonvolatile memory such as read only memory (ROM) and/or random access memory (RAM). By way of example, and not limitation, system memory 30' may also include an operating system, application programs, other program modules, and program data.

A user can interface with (for example, enter commands and information) the computer 10' through input devices 50'. A monitor or other type of device can also be connected to the system bus 22' via an interface, such as an output interface 360. The computer may include a database 40'. In addition to a monitor, computers may also include other peripheral output devices. The computer 10' may operate in a networked or distributed environment using logical connections to one or more other remote device(s) 80' such as other computers. The logical connections may include network interface(s) 70' to a network, such as a local area network (LAN), a wide area network (WAN), and/or a global computer network, but may also include other networks/buses.

Information handling device circuitry, as for example outlined in FIG. 8, may be used in client devices such as a personal desktop computer, a laptop computer, or smaller devices such as a tablet or a smart phone. In the latter cases, i.e., for a tablet computer and a smart phone, the circuitry outlined in FIG. 8 may be adapted to a system on chip type circuitry. The device, irrespective of the circuitry provided, may provide and receive data to/from another device, e.g., a server or system that coordinates with various other systems. As will be appreciated by one having ordinary skill in the art, other circuitry or additional circuitry from that outlined in the example of FIG. 8 may be employed in various electronic devices that are used in whole or in part to implement the systems, methods and products of the various embodiments described herein.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium, such as a non-signal storage device, and that are executed by a processor. A storage device may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random-access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a storage device is not a signal and "non-transitory" includes all media except signal media.

Program code embodied on a storage medium may be transmitted using any appropriate medium, including but not limited to wireless, wireline, optical fiber cable, RF, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and program products according to various example embodiments. It will be understood that the actions and functionality may be implemented at least in part by program instructions. These program instructions may be provided to a processor of a device, a special purpose information handling device, or other programmable data processing device to produce a machine, such that the instructions, which execute via a processor of the device implement the functions/acts specified.

It is worth noting that while specific blocks are used in the figures, and a particular ordering of blocks has been illustrated, these are non-limiting examples. In certain contexts, two or more blocks may be combined, a block may be split into two or more blocks, or certain blocks may be re-ordered or re-organized as appropriate, as the explicit illustrated examples are used only for descriptive purposes and are not to be construed as limiting.

As used herein, the singular "a" and "an" may be construed as including the plural "one or more" unless clearly indicated otherwise.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. An assistive robot apparatus, the assistive robot apparatus comprising:

a sensor system comprising at least one sensor that obtains input related to a health metric of a person under care of the assistive robot apparatus, wherein the health metric indicates a health state of the person under care;

an actuator system comprising at least one actuator that causes at least a portion of the assistive robot apparatus to move and interact with an environment of the assistive robot apparatus responsive to detecting, utilizing the sensor system, the input related to the health metric indicates the person under care needs assistance from the assistive robot apparatus, wherein the actuator system provides movement to the assistive robot apparatus that transforms the assistive robot apparatus from a first assistive state having a first object appearance to a second assistive state having a second object appearance different than the first object appearance, wherein the transformation assists the person under care, wherein at least one of the first object appearance or the second object appearance appears as a piece of furniture;

an analysis system that analyzes the input and provides instructions to the actuator system based upon the input, wherein the analysis system learns, using at least one learning technique, information about the person under care over time and continually modifies default values of the analysis system based upon the information about the person under care learned over time to create values unique to the person under care, and wherein the analyzing the input is performed in view of the modified default values and wherein the instructions for the actuator system are unique to the person under care to provide movements by the actuator system for the person under care based upon the learned information about the person under care, wherein the analysis system identifies a condition of the person under care based upon the health state, wherein the second assistive state comprises an assistive state to address the health state of the person under care, and wherein the analysis system provides instructions to the actuator system to perform movements to address the health state; and an output system comprising at least one output device that communicates with at least one other system.

2. The assistive robot apparatus of claim 1, wherein the at least one sensor is located on the assistive robot apparatus.

3. The assistive robot apparatus of claim 1, wherein the first object appearance appears as a piece of furniture and holds the person under care.

4. The assistive robot apparatus of claim 1, wherein the analysis system identifies a status of the person under care from the input.

5. The assistive robot apparatus of claim 4, wherein to identify the status of the person under care, the analysis system analyzes the input against a datastore of inputs unique to the person under care.

6. The assistive robot apparatus of claim 1, wherein the analysis system comprises at least one machine-learning model.

7. The assistive robot apparatus of claim 6, wherein the at least one machine-learning model is trained based upon inputs of the person under care and provides instructions based upon the person under care.

8. The assistive robot apparatus of claim 1, wherein the at least output device provides instructions to another apparatus within an Internet of Things to perform a function based upon the input and the analysis.

9. The assistive robot apparatus of claim 1, wherein the at least one output device provides at least one notification to at least one user regarding a status of the person under care based upon the input.

10. The assistive robot apparatus of claim 1, wherein the at least one output device provides output to at least one other assistive robot apparatus.

11. A method, the method comprising:

obtaining, using a sensor system of an assistive robot apparatus, input related to a health metric of a person under care of the assistive robot apparatus, wherein the health metric indicates a health state of the person under care;

analyzing, using an analysis system of the assistive robot apparatus, the input, wherein the analysis system learns, using at least one learning technique, information about the person under care over time and continually modifies default values of the analysis system based upon the information about the person under care learned over time to create values unique to the person under care, and wherein the analyzing the input is performed in view of the modified default values;

providing, from the analysis system, instructions to an actuator system of the assistive robot apparatus based upon the input, wherein the instructions for the actuator system are unique to the person under care to provide movements by the actuator system for the person under care based upon the learned information about the person under care, wherein the analysis system identifies a condition of the person under care based upon the health state, wherein the second assistive state comprises an assistive state to address the health state of the person under care, and wherein the analysis system provides instructions to the actuator system to perform movements to address the health state;

interacting with an environment of the assistive robot apparatus in view of the input and by activating at least one actuator of the actuator system causing at least a portion of the assistive robot system to move based upon the instructions and responsive to detecting, utilizing the sensor system, the input related to the health metric indicates the person under care needs assistance from the assistive robot apparatus, wherein the actuator system provides movement to the assistive robot apparatus that transforms the assistive robot apparatus from a first assistive state having a first object appearance to a second assistive state having a second object appearance different than the first object appearance, wherein the transformation assists the person under care, wherein at least one of the first object appearance or the second object appearance appears as a piece of furniture; and communicating, using at least one output device of an output system of the assistive robot apparatus, with at least one other system based upon the input.

12. The method of claim 11, wherein the obtaining comprises obtaining the input from at least one sensor is located on the assistive robot apparatus.

13. The method of claim 11, wherein the interacting comprises wherein the first object appearance appears as a piece of furniture and holds the person under care.

14. The method of claim 11, wherein the analyzing comprises identifying a status of the person under care from the input.

15. The method of claim 14, wherein the identifying the status of the person under care comprises analyzing the input against a datastore of inputs unique to the person under care.

16. The method of claim 11, wherein the analyzing comprises utilizing at least one machine-learning model.

17. The method of claim 16, wherein the at least one machine-learning model is trained based upon inputs of the person under care and provides instructions based upon the person under care.

18. The method of claim 11, wherein the communicating comprises providing instructions to another apparatus within an Internet of Things to perform a function based upon the input and the analysis.

19. The method of claim 11, wherein the communicating comprises providing at least one notification to at least one user regarding a status of the person under care based upon the input.

20. A product, the product comprising:

a non-transitory computer-readable storage device that stores executable code that, when executed by a processor, causes the product to:

obtain, using a sensor system of an assistive robot apparatus, input related to a health metric of a person under care of the assistive robot apparatus, wherein the health metric indicates a health state of the person under care;

analyze, using an analysis system of the assistive robot apparatus, the input, wherein the analysis system learns, using at least one learning technique, information about the person under care over time and continually modifies default values of the analysis system based upon the information about the person under care learned over time to create values unique to the person under care, and wherein the analyzing the input is performed in view of the modified default values;

provide, from the analysis system, instructions to an actuator system of the assistive robot apparatus based upon the input, wherein the instructions for the actuator system are unique to the person under care to provide movements by the actuator system for the person under care based upon the learned information about the person under care, wherein the analysis system identifies a condition of the person under care based upon the health state, wherein the second assistive state comprises an assistive state to address the health state of the person under care, and wherein the analysis system provides instructions to the actuator system to perform movements to address the health state;

interact with an environment of the assistive robot apparatus in view of the input and by activating at least one actuator of the actuator system causing at least a portion of the assistive robot system to move based upon the instructions and responsive to detecting, utilizing the sensor system, the input related to the health metric indicates the person under care needs assistance from the assistive robot apparatus, wherein the actuator system provides movement to the assistive robot apparatus that transforms the assistive robot apparatus from a first assistive state having a first object appearance to a second assistive state having a second object appearance different than the first object appearance, wherein the transformation assists the person under care, wherein at least one of the first object appearance or the second object appearance appears as a piece of furniture; and communicate, using at least one output device of an output system of the assistive robot apparatus, with at least one other system based upon the input.

* * * * *